US009901288B2

(12) United States Patent
Gollar

(10) Patent No.: US 9,901,288 B2
(45) Date of Patent: Feb. 27, 2018

(54) METHODS OF DETECTING GASEOUS COMPONENT LEVELS IN A BREATH

(75) Inventor: Edward Gollar, Cincinnati, OH (US)

(73) Assignee: OmegaPoint Systems, LLC, Cincinnati, OH (US)

(*) Notice: Subject to any disclaimer, the term of this patent is extended or adjusted under 35 U.S.C. 154(b) by 2032 days.

(21) Appl. No.: 12/886,725

(22) Filed: Sep. 21, 2010

(65) Prior Publication Data

US 2011/0009765 A1  Jan. 13, 2011

Related U.S. Application Data

(63) Continuation-in-part of application No. 11/182,402, filed on Jul. 15, 2005, which is a continuation-in-part of application No. 10/097,460, filed on Mar. 14, 2002, now abandoned.

(51) Int. Cl.
| | |
|---|---|
| *A61B 5/08* | (2006.01) |
| *A61B 5/097* | (2006.01) |
| *B60K 28/06* | (2006.01) |
| *G01N 33/497* | (2006.01) |
| *A61B 5/087* | (2006.01) |
| *A61B 5/117* | (2016.01) |

(52) U.S. Cl.
CPC ............ *A61B 5/097* (2013.01); *B60K 28/063* (2013.01); *G01N 33/4972* (2013.01); *A61B 5/0878* (2013.01); *A61B 5/117* (2013.01); *B60W 2540/24* (2013.01)

(58) Field of Classification Search
CPC .. G01N 33/4972; Y10S 436/90; B60K 28/063
USPC .................................. 600/529, 532; 73/23.3
See application file for complete search history.

(56) References Cited

U.S. PATENT DOCUMENTS

| | | | |
|---|---|---|---|
| 3,940,251 A | 2/1976 | Jones et al. | |
| 3,949,739 A * | 4/1976 | Rodder ........................ | 600/538 |
| 3,966,579 A | 6/1976 | Chang et al. | |
| 4,093,945 A | 6/1978 | Collier et al. | |
| 4,297,871 A | 11/1981 | Wright et al. | |
| 4,300,385 A * | 11/1981 | Albarda ........................ | 73/23.3 |
| 4,443,791 A | 4/1984 | Risgin et al. | |

(Continued)

OTHER PUBLICATIONS

Canadian Office Action dated Apr. 7, 2014 relating to CA Patent Application No. 2,552,130; (5 pages).

*Primary Examiner* — Patricia Mallari
*Assistant Examiner* — Michael Catina
(74) *Attorney, Agent, or Firm* — Dinsmore & Shohl LLP

(57) ABSTRACT

Method for detecting gaseous component levels in a breath, comprising: receiving a breath through a breath channel, wherein the breath channel is in fluid communication with a flow rate sensor and an electrochemical fuel cell gas sensor; measuring a flow rate of the breath received through the breath channel; measuring a first time, wherein the first time corresponds to an amount of time elapsed while receiving the breath in the breath channel; and calculating a current gaseous component level utilizing the flow rate, first time and an output from the gas sensor. Methods for detecting an error condition while measuring gaseous component levels in a breath comprising: determining if the peak output occurs while breath is still being received in the breath channel; and if the peak output occurs while breath is still being received in the breath channel, alerting a user of an error condition.

15 Claims, 4 Drawing Sheets

(56) References Cited

U.S. PATENT DOCUMENTS

| | | | |
|---|---|---|---|
| 4,487,055 A | 12/1984 | Wolf | |
| 4,707,336 A | 11/1987 | Jones | |
| 4,749,553 A | 6/1988 | Lopez et al. | |
| 4,770,026 A | 9/1988 | Wolf | |
| 4,868,545 A | 9/1989 | Jones | |
| 4,914,038 A | 4/1990 | Jewitt | |
| 4,926,164 A | 5/1990 | Porter et al. | |
| 4,996,161 A * | 2/1991 | Conners et al. | 436/132 |
| 5,020,628 A * | 6/1991 | Bigliardi et al. | 180/272 |
| 5,048,321 A * | 9/1991 | Chow | 73/23.3 |
| 5,303,575 A | 4/1994 | Brown et al. | |
| 5,393,495 A | 2/1995 | Forrester | |
| 5,426,416 A | 6/1995 | Jefferies et al. | |
| 5,458,853 A | 10/1995 | Porter et al. | |
| 5,726,906 A | 3/1998 | Matthiessen et al. | |
| 5,739,412 A | 4/1998 | Stock et al. | |
| 5,929,319 A | 7/1999 | King et al. | |
| 6,026,674 A * | 2/2000 | Gammenthaler | 73/19.01 |
| 6,085,576 A | 7/2000 | Sunshine et al. | |
| 6,135,967 A * | 10/2000 | Fiorenza et al. | 600/529 |
| 6,167,746 B1 | 1/2001 | Gammenthaler | |
| 6,234,006 B1 | 5/2001 | Sunshine et al. | |
| 6,418,783 B2 | 7/2002 | Sunshine et al. | |
| 6,464,941 B1 | 10/2002 | Diekmann | |
| 6,596,153 B1 | 7/2003 | Traylor, III | |
| 6,658,915 B2 | 12/2003 | Sunshine et al. | |
| 6,792,793 B2 | 9/2004 | Mendoza | |
| 6,795,775 B2 | 9/2004 | Traylor, III | |
| 6,853,956 B2 | 2/2005 | Ballard, Jr. et al. | |
| 6,883,364 B2 | 4/2005 | Sunshine et al. | |
| 7,122,154 B1 * | 10/2006 | Forrester et al. | 422/84 |
| 7,421,882 B2 * | 9/2008 | Leddy et al. | 73/23.3 |

* cited by examiner

METHODS OF DETECTING GASEOUS COMPONENT LEVELS IN A BREATH

CROSS REFERENCE TO RELATED APPLICATIONS

This application is a continuation-in-part of U.S. Ser. No. 11/182,402, filed on Jul. 15, 2005 which is a continuation-in-part of U.S. Ser. No. 10/097,460, filed on Mar. 14, 2002, the entire disclosures of which are hereby incorporated by reference.

TECHNICAL FIELD

The present invention relates to the field of gaseous breath detection systems, and methods for using the same, and more particularly, to the field of portable personal gaseous breath detection apparatus and methods for using same.

BACKGROUND OF THE INVENTION

Blood alcohol content, or BAC, is expressed as a percent and is defined as grams of alcohol per 100 milliliters of blood. A person's blood alcohol content can be determined by measuring the alcohol content of his breath. The assumption is then made that the ratio by mass of the alcohol content of the blood to that of the breath is 2100:1.

There are several methods that use a person's breath to determine his BAC. A common method is to use a tin-oxide semiconductor alcohol sensor that is exposed to a person's breath. It has the advantage of low cost at the expense of accuracy, alcohol specificity, and electrical power consumption. Another method is to employ the use of an electrochemical fuel cell alcohol sensor. While this type of sensor tends to be more accurate, more alcohol specific, and utilizes less electrical power, the sensor itself is significantly more expensive and has traditionally required the use of an active sampling mechanism, such as a pump, that samples a predetermined volume of breath. For example, Gammenthaler (U.S. Pat. No. 6,026,674) discloses an apparatus for determining the alcohol concentration in a gaseous mixture. The apparatus utilizes a fuel cell and a valve. The valve diverts a portion of the breath flow into the fuel cell thereby indicating and ensuring that a predefined amount of breath flow has passed through the fuel cell. The predetermined volume is calculated by integrating breath flow over time with the valve open and then closing the valve when the predetermined limit is reached. An electrochemical sensor responds differently to varying volumes of an alcohol gas sample. Since the traditional sampling mechanism samples a predetermined and constant volume of breath, the method for calculating the alcohol content of the breath does not need to take into account the total exhaled volume of breath, as does an apparatus without a sampling mechanism that allows for varying volumes of breath.

Chang et al. (U.S. Pat. No. 3,966,579) disclose an apparatus for measuring alcohol concentrations utilizing an electrochemical fuel cell alcohol sensor without an active sampling mechanism. Chang et al. monitor alcohol concentrations present in a gaseous breath by measuring the magnitude of the short circuit passing through the external circuit between the anode and cathode of the fuel cell. However, Chang et al. fail to disclose a method for detecting and calculating gaseous component levels of the breath which accounts for volume of the breath received.

In addition, it is desirable to discriminate components different from ethanol in breath samples. These contaminants can lead to error conditions such as faulty readings. For example, it is known that cigarette or cigar smoke can cause fuel cell gas sensors to report inaccurate gas component levels. Other error conditions could be elevated readings due to other volatile components in the breath. Chow (U.S. Pat. No. 5,048,321) discloses a method of discriminating alcohols different from ethanol in breath samples.

Accordingly, it is desirable to have a breath detection method and apparatus that utilizes an electrochemical fuel cell alcohol sensor for accuracy, alcohol specificity, and low power consumption, and eliminates the need for a sampling mechanism, saving more in cost, power consumption, and size. However, eliminating the sampling mechanism requires an improved method of calculating the alcohol content of the breath that takes into account the total exhaled volume of breath. In addition, since an electrochemical sensor in an apparatus without a sampling mechanism can respond to gases other than alcohol that are typically found in expired cigarette, cigar, or pipe smoke and cause an error condition in the fuel cell, a method of detecting such an error condition is also desired.

SUMMARY OF THE INVENTION

The present invention is directed to methods for detecting gaseous component levels in a breath. More particularly, the invention is directed to methods for detecting gaseous component levels in a breath received through a breath channel utilizing an electrochemical fuel cell gas sensor.

One embodiment of the present invention comprises a method for detecting gaseous component levels in a breath. The method comprises: receiving a breath through a breath channel, wherein the breath channel is in fluid communication with a flow rate sensor and an electrochemical fuel cell gas sensor; measuring a flow rate of the breath received through the breath channel; measuring a first time, wherein the first time corresponds to an amount of time elapsed while receiving the breath in the breath channel; and calculating a current gaseous component level utilizing the flow rate, first time and an output from the gas sensor.

Another embodiment of the present invention is a method for detecting an error condition while measuring gaseous component levels in a breath. The method comprises: receiving a breath through a breath channel, wherein the breath channel is in fluid communication with a flow rate sensor and an electrochemical fuel cell gas sensor; measuring a flow rate of the breath received through the breath channel; measuring a first time, wherein the first time corresponds to an amount of time elapsed while receiving the breath in the breath channel; measuring a peak output from the gas sensor; determining if the peak output occurs while breath is still being received in the breath channel; and if the peak output occurs while breath is still being received in the breath channel, alerting a user of an error condition.

Yet another embodiment of the present invention comprises a computer program product comprising a computer readable medium carrying instructions for allowing a computer system to detect gaseous component levels in a breath received through a breath channel. The instructions comprising a method of: measuring a flow rate of the breath received through the breath channel; measuring a first time, wherein the first time corresponds to an amount of time elapsed while receiving the breath in the breath channel; and calculating a current gaseous component level utilizing the flow rate, first time and an output from an electrochemical fuel cell gas sensor in fluid communication with the breath.

Another embodiment of the present invention comprises a computer program product comprising a computer readable medium carrying instructions for allowing a computer system to detect an error condition while measuring gaseous component levels in a breath received through a breath channel. The instructions comprising a method of: measuring a flow rate of the breath received through the breath channel; measuring a first time, wherein the first time corresponds to an amount of time elapsed while receiving the breath in the breath channel; measuring a peak output from the gas sensor; determining if the peak output occurs while breath is still being received in the breath channel; and if the peak output occurs while breath is still being received in the breath channel, alerting a user of an error condition.

One embodiment of the present invention comprises a propagated computer data signal transmitted via a propagation medium. The computer data signal comprising a plurality of instructions for detecting gaseous component levels in a breath received through a breath channel. The plurality of instructions, when executed by a processor, cause the processor to perform the act of: measuring a flow rate of the breath received through the breath channel; measuring a first time, wherein the first time corresponds to an amount of time elapsed while receiving the breath in the breath channel; and calculating a current gaseous component level utilizing the flow rate, first time and an output from an electrochemical fuel cell gas sensor in fluid communication with the breath.

Yet another embodiment of the present invention comprises a propagated computer data signal transmitted via a propagation medium. The computer data signal comprises a plurality of instructions for detecting gaseous component levels in a breath received through a breath channel. The plurality of instructions, when executed by a processor, cause the processor to perform the act of: measuring a flow rate of the breath received through the breath channel; measuring a first time, wherein the first time corresponds to an amount of time elapsed while receiving the breath in the breath channel; measuring a peak output from the gas sensor; determining if the peak output occurs while breath is still being received in the breath channel; and if the peak output occurs while breath is still being received in the breath channel, alerting a user of an error condition.

Still other advantages of the present invention will become apparent to those skilled in this art from the following description wherein there is shown and described exemplary embodiments of this invention, including a best mode currently contemplated for the invention, simply for purposes of illustration. As will be realized, the invention is capable of other different aspects and embodiments without departing from the scope of the invention.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

Figure 1:
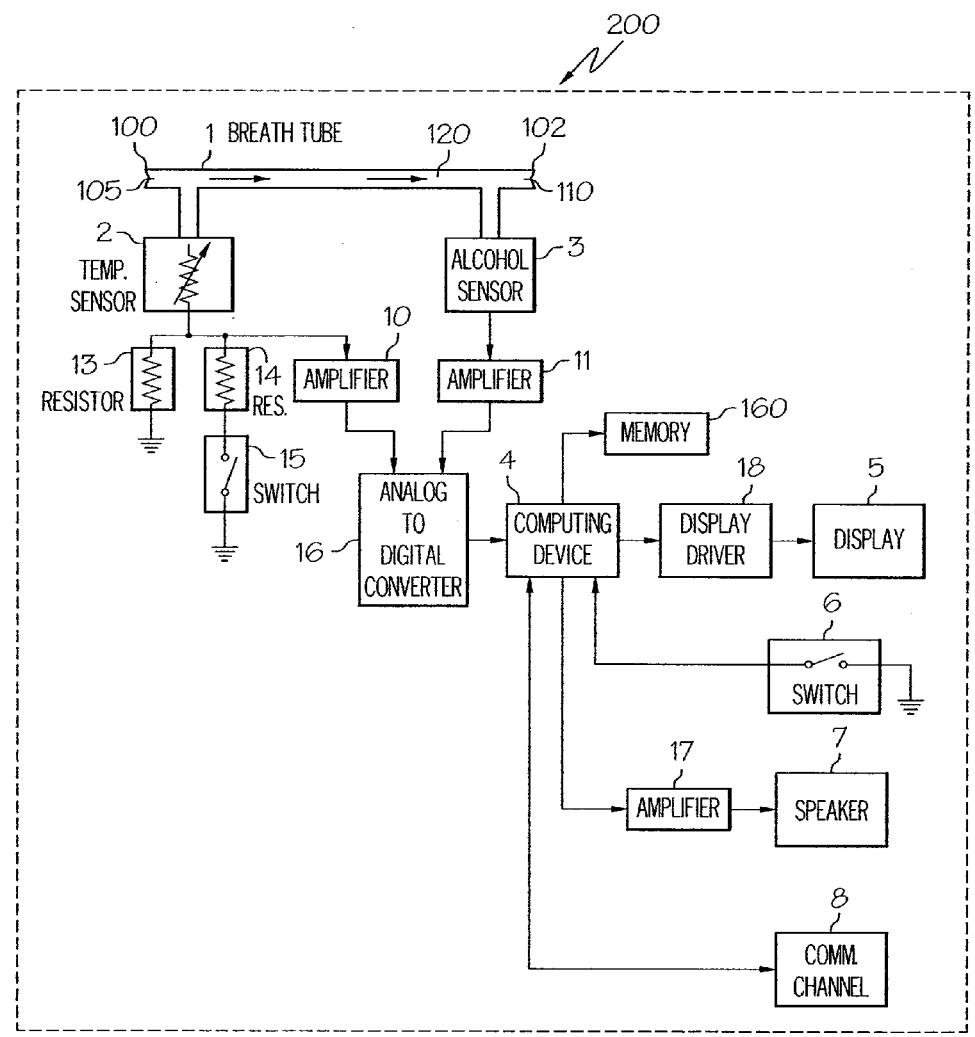
FIG. 1 is a schematic illustration of an exemplary breath alcohol tester apparatus according to a first embodiment of the present invention.

The embodiments set forth in the drawings are illustrative in nature and are not intended to be limiting of the invention defined by the claims. Moreover, individual features of the drawings and the invention will be more fully apparent and understood in view of the detailed description.

DETAILED DESCRIPTION OF THE INVENTION

Reference will now be made in detail to the present exemplary embodiments of the invention, examples of which are illustrated in the accompanying drawings, wherein like numerals indicate the same elements throughout the views.

Referring to FIG. 1, the personal breath tester 200 comprises a breath passage 1 having a flowpath 120, a proximal end 100 and a distal end 102, wherein the proximal end 100 comprises an inlet 105 for accepting a person's breath and the distal end 102 comprises an outlet 110 for venting the breath. A temperature sensor 2 is in fluid communication with the flowpath 120 of the breath passage 1. In addition, an alcohol sensor 3 is in fluid communication with the flowpath 120 of the breath passage 1. In an exemplary embodiment, the temperature sensor 2 and/or alcohol sensor 3 are physically contained within the flowpath 120 of the breath passage 1. Since the alcohol sensor 3 is in fluid communication with the flowpath 120, the need for a mechanical pump or sampling system is eliminated.

In one exemplary embodiment, the temperature sensor 2 comprises a thermistor sensor and the alcohol sensor 3 comprises an electrochemical fuel cell with an ethanol sensor. The temperature sensor 2 is in electrical communication with two resistors 13 and 14. The resistor 14 is in electrical communication with an electrical switch 15, which in turn is in electrical communication with a computing device 4. The temperature sensor 2 is also in electrical communication to an amplifier 10 for generating a signal representative of flow rate. The output signal of the flow amplifier 10 is in electrical communication with the analog-to-digital converter 16, which converts the output signal into a digital number that can be interpreted by the computing device 4, such as a microprocessor.

The alcohol sensor 3 is in electrical communication with an amplifier 11. The output signal of the amplifier is in electrical communication with the analog-to-digital converter 16, which converts the output signal into a digital number. The output signal of the analog-to-digital converter is connected to the computing device 4.

A display 5, which in one exemplary embodiment comprises an alphanumeric display, is driven by a display driver circuit 18. The display driver circuit 18 is in electrical communication and is controlled by the computing device 4. In another exemplary embodiment, the present invention further comprises a speaker 7, which is controlled by an amplifier 17, wherein the amplifier is controlled by the computing device 4. A momentary switch 6 and a communication channel 8 are in electrical communication with the computing device 4.

Figure 2A:
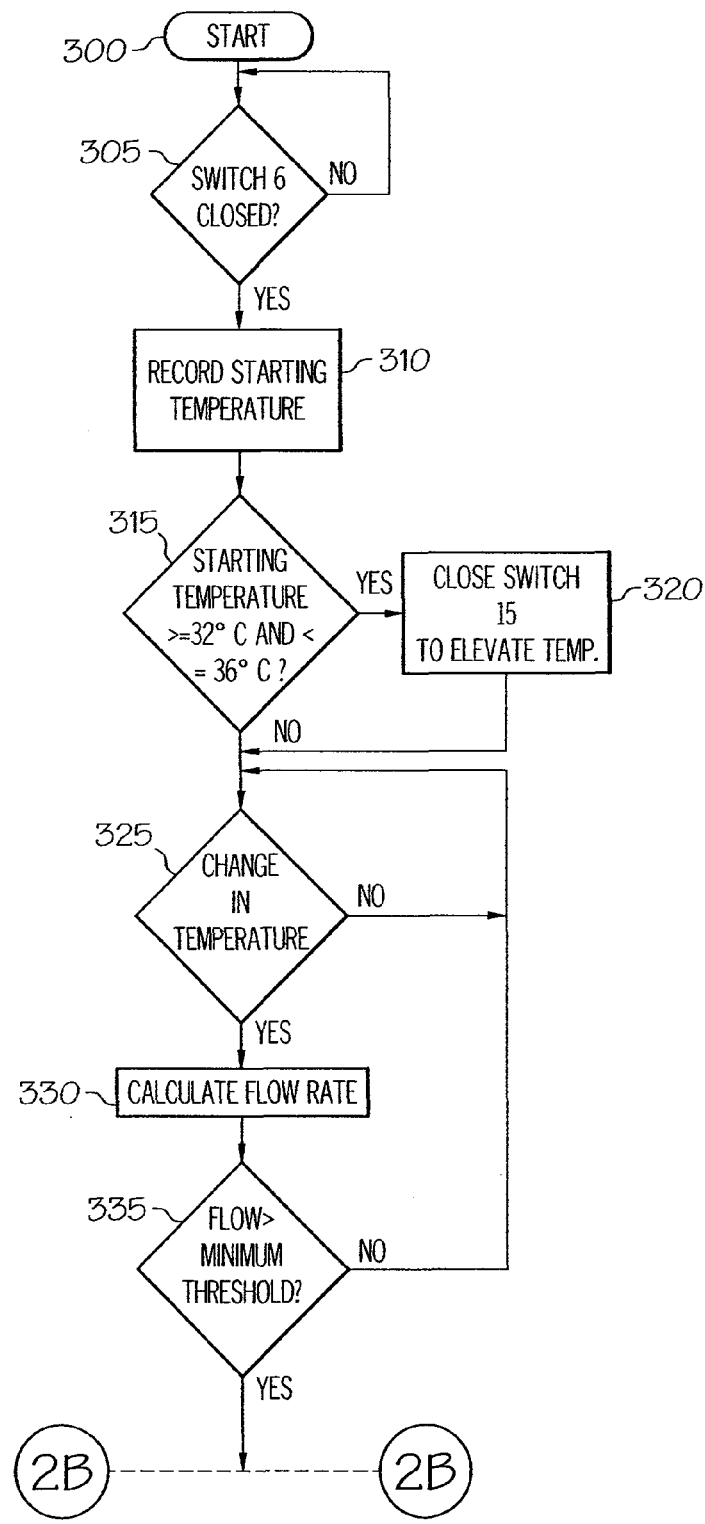
FIG. 2 is a flowchart depicting an exemplary embodiment of the method of detecting breath alcohol levels according to a second embodiment of the present invention.
Figure 2B:
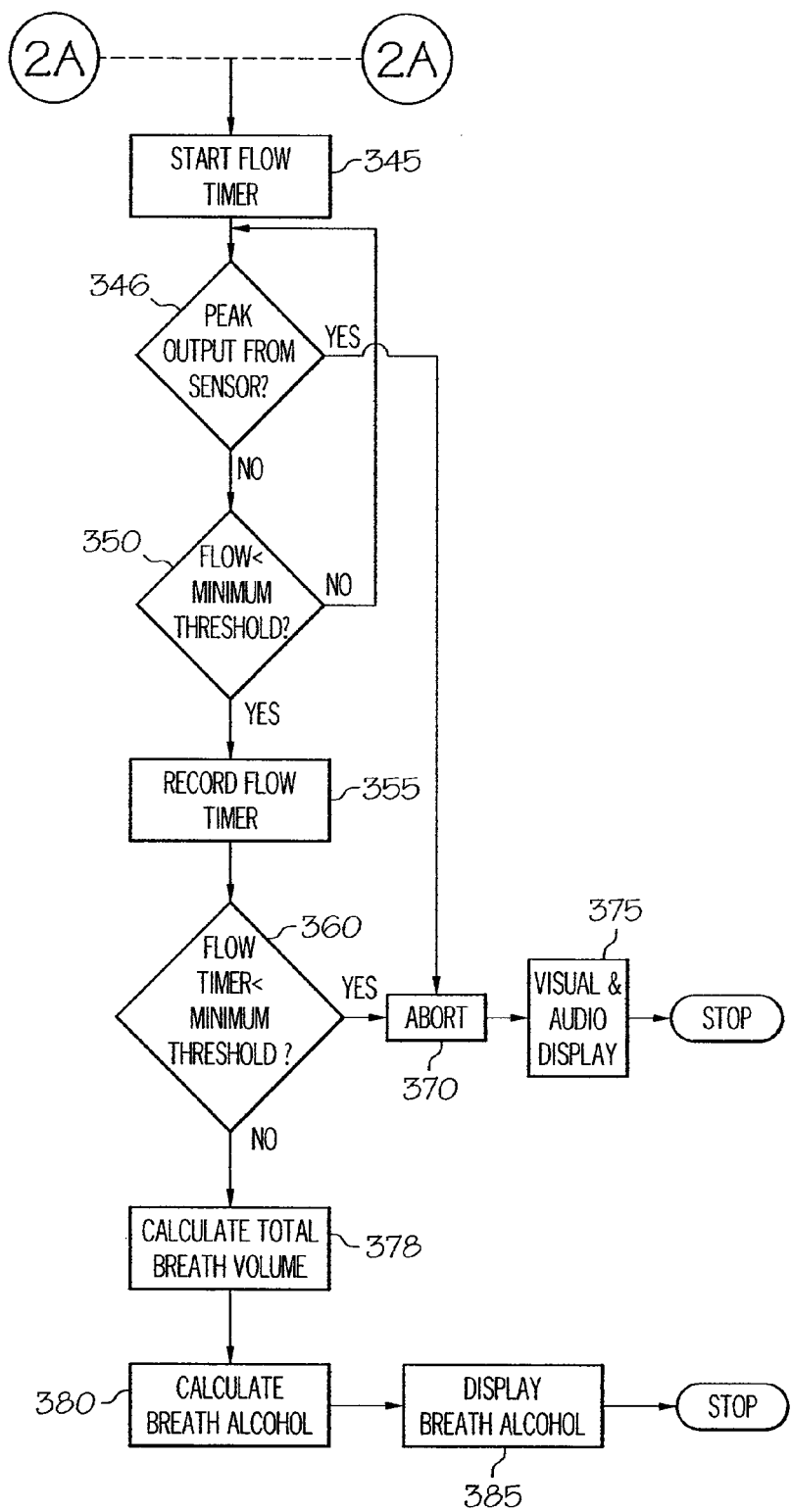

In one exemplary embodiment of the present invention depicted by FIG. 2, a breath test is initiated when a person depresses the switch 6 (step 305) of the personal breath tester 200. When the computing device 4 determines that the switch 6 has been depressed, the computing device 4 obtains the initial temperature of the temperature sensor 2 by opening the switch 15, converting the temperature sensor 2 output signal into a digital number with the analog-to-digital converter 16, and recording that number as the starting value of the temperature sensor 2 (step 310). If the recorded starting value of the temperature sensor 2 is less than 32° C. or greater than 36° C., the switch 15 is left open and the personal breath tester 200 is ready to begin testing breath samples. If the recorded starting value is equal to or more than 32° C. and less than or equal to 36° C. (step 315), then switch 15 is turned on (closes circuit) by the computing device 4 (step 320) to increase the temperature level to that greater than expected human breath (i.e. 34° C.).

When switch 15 is turned on, the resistor 14 is placed in electrical communication with the temperature sensor 2, causing a significant increase in current to flow through the temperature sensor 2. After a short amount of time, this causes heating of the temperature sensor 2, and the internal temperature will rise significantly above 34° C.

Once a suitable initial temperature has been obtained (i.e. less than 32° C. or greater than 36° C.), whether switch 15 is on or off, a person blows into the breath passage 1 of the personal breath detector 200. The temperature of the person's breath is typically 34° C. The stream of air blown into the breath passage will cause the temperature of the temperature sensor 2 to change.

If the initial temperature of the temperature sensor 2 immediately before blowing is below 32° C., then the temperature will rise with blowing. Similarly, if the initial temperature of the temperature sensor 2 is above 36° C., then the temperature will fall with blowing.

This change in temperature is amplified by the flow amplifier 10, converted into a digital signal by the analog-to-digital converter 16, and then sent to the computing device 4. The change in temperature is an indication that the user is blowing, and the rate at which this temperature change occurs is an indication of the flow rate (step 325). A quick change in temperature indicates a higher flow rate than a slow change in temperature.

The computing device 4 calculates the flow rate (step 330) and compares it to a minimum flow threshold value, which is stored in the computing device or computer readable memory unit 160. If the flow rate is higher than the minimum (step 335), then the computing device 4 starts an internal flow timer (step 345). While the person is blowing, the alcohol sensor output is continually checked to see if it peaks and then drops before blowing stops (step 346). If it does peak, indicating the presence of exhaled cigarette, cigar, or pipe smoke, then the computing device 4 aborts the breath test (step 370), and sends a visual abort indication to the user. In one exemplary embodiment, the abort indication is a visual indication on the personal breath tester (i.e., such as a display 5). In another exemplary embodiment, the abort indicator is an audible signal through a speaker 7. If the alcohol sensor peaks, then another breath test must be initiated by the person. Once the person stops blowing air into the breath passage and/or the air flow rate drops below the minimum threshold value (step 350), then the computing device 4 records the flow timer value as an indication of how long the person was blowing air into the breath passage at an acceptable rate (i.e. above minimum threshold value) (step 355). If the recorded flow timer value is less than a minimum timer threshold value (step 360), stored in the computing device, then the computing device 4 aborts the breath test (step 370), and sends a visual abort indication to the user. In one exemplary embodiment, the abort indication is a visual indication on the personal breath tester (i.e., such as a display 5). In another exemplary embodiment, the abort indicator is an audible signal through a speaker 7 (step 375). If the recorded flow timer value is less than the minimum timer threshold another breath test must be initiated by the person. The minimum flow rate and flow timer threshold values exist to insure that the person taking the test is providing a minimum volume of deep-lung (alveolar) air into the device.

As long as the minimum flow rate and flow timer threshold values are exceeded, the computing device 4 calculates the total breath volume by integrating the breath flow rate over time (step 378). In one exemplary embodiment, the fuel cell alcohol sensor sends a signal to the amplifier 11. The amplifier 11 sends an amplified signal to the analog/digital converter 16. The analog/digital converter 16 sends the digital signal to the computing device 4. The computing device 4 then calculates an equivalent breath alcohol level using a method incorporating the total breath volume and the output signal of the fuel cell alcohol sensor. The breath alcohol level is then indicated on the display 5 as a digital number (step 385), along with an audible indication on speaker 7 that the test is completed.

Figure 3:
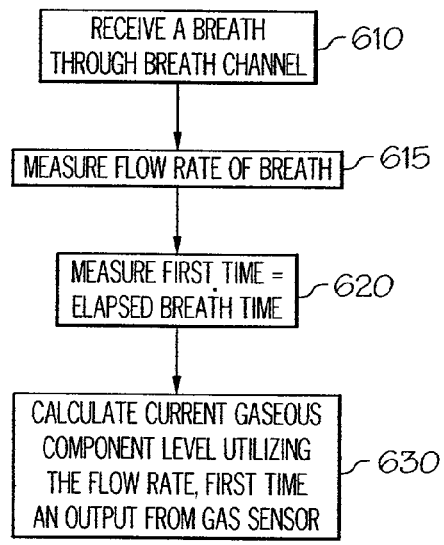
FIG. 3 is a flowchart depicting an exemplary method of detecting breath alcohol levels according to a third embodiment of the present invention.

Another embodiment of the present invention, as illustrated in FIG. 3, is a method for detecting gaseous component levels in a breath. The method comprises: a breath being received through the breath channel (610). The breath channel is in fluid communication with a flow rate sensor and an electrochemical fuel cell gas sensor. The flow rate of the received breath is measured (615). A first time is measured (620). The first time corresponds to the amount of time elapsed while receiving the breath in the breath channel. A current gaseous component level of the breath received in the breath channel is calculated utilizing the flow rate, first time and an output from the gas sensor (630). In one exemplary embodiment, the gaseous component is alcohol. In another exemplary embodiment, the flow rate sensor comprises a pressure sensor. In an alternative embodiment, the flow rate sensor comprises a temperature sensor.

In another embodiment of the present invention, calculating the current gaseous component level further comprises calculating a volume of breath received based on the flow rate and the first time.

In one exemplary embodiment, the method further comprises measuring the flow rate at a plurality of time intervals and calculating the volume of breath based on the plurality of flow rates and time intervals. For example, in one embodiment, the flow rate may be measured from about every 0.001 seconds to about every 1 second. In another exemplary embodiment, the flow rate is measured every 0.1 seconds and stored on the apparatus for later retrieval when calculating the volume of breath received.

In one exemplary embodiment, the method used to calculate the breath alcohol level takes the form of an equation. The alcohol sensor output is directly proportional to the actual breath alcohol level but increases with breath volume, so there has to be an inversely proportional relationship between the sensor output and breath volume, so that different volumes of breath will result in the same BAC calculation for the same actual breath alcohol level. Thus the equation takes the form:

$$BAC = S/V * K,$$

wherein:
BAC is the blood alcohol content, in %;
S is the output of the alcohol sensor amplifier, in volts;
V is the volume of breath, in liters; and K is a constant used to convert the calculated units into the BAC, in %-liters/volts, and is derived empirically.

While the equation above indicates a linear (or first order) relationship between BAC, the sensor output S and the breath volume V, in reality the relationship between these variables is more complex and, in another embodiment, can be approximated by an equation of the second order or higher. Thus the equation becomes:

$$BAC=(S^2*A_S+S*B_S+C_S)*(V^2*A_V+V*B_V+C_V),$$

wherein:

$A_S$, $B_S$, $C_S$, $A_V$, $B_V$ and $C_V$ are constants that are derived empirically. These constants can be determined by performing a series of breath alcohol tests, and changing one variable while keeping the other variable constant. This will result in a set of data points for BAC and the changing variable showing the relationship between the two. Then a curve fitting algorithm, such as that of a least squares polynomial fit, in the form of a computer program that is commonly available for purchase, can be applied to the data. The program will calculate the constants A, B and C for the changing variable. For example, a series of breath tests can be performed using an alcohol simulator set to different BAC levels using a fixed volume of breath (V). A series of data points for the BAC and the sensor output (S) will then be collected, and the constants $A_S$, $B_S$, $C_S$ can be calculated by the curve fit program.

In another exemplary embodiment, the method further comprises measuring a second time, wherein the second time corresponds to an elapsed time from the time corresponding to when the breath has ceased being received in the breath channel to the time corresponding to the peak output from the gas sensor. The second time can be utilized to further enhance the calculation of the current gaseous component level.

In this exemplary embodiment, the alcohol sensor output is directly proportional to the actual breath alcohol level but increases with breath volume, so there has to be an inversely proportional relationship between the sensor output and breath volume, so that different volumes of breath will result in the same BAC calculation for the same actual breath alcohol level. The alcohol sensor output decreases with an increase in the second time (a characteristic of some fuel cell sensors that is largely due to environmental variables), so there has to be a directly proportional relationship between the sensor output and the second time, so that different values of the second time will result in the same breath alcohol level calculation for the same actual breath alcohol level. Thus the equation takes the form:

$$BAC=P/V*T*K$$

wherein:
BAC is the blood alcohol content, in %.
P is the alcohol sensor peak output, in volts;
V is the calculated volume of breath, in liters;
T is the second time, in seconds; and
K is a constant used to convert the calculated units into the BAC, in %-liters/volts-sec, and is derived empirically.

While the equation above indicates a linear (or first order) relationship between BAC, the sensor output S, the volume V, and the time T, in reality the relationship between these variables is more complex and, in another embodiment, can be approximated by the second order or higher. Thus the equation becomes:

$$BAC=(P^2*A_S+P*B_S+C_S)*(V^2*A_V+V*B_V+C_V)*(T^2*A_T+T*B_T+C_T),$$

wherein:

$A_S$, $B_S$, $C_S$, $A_V$, $B_V$, $C_V$, $A_T$, $B_T$ and $C_T$ are constants that are derived empirically, and can be determined by the method described previously.

In another embodiment the second time corresponds to an elapsed time starting from any fixed time after the breath has started to be received in the breath channel to the time corresponding to the peak output from the gas sensor.

Figure 4:
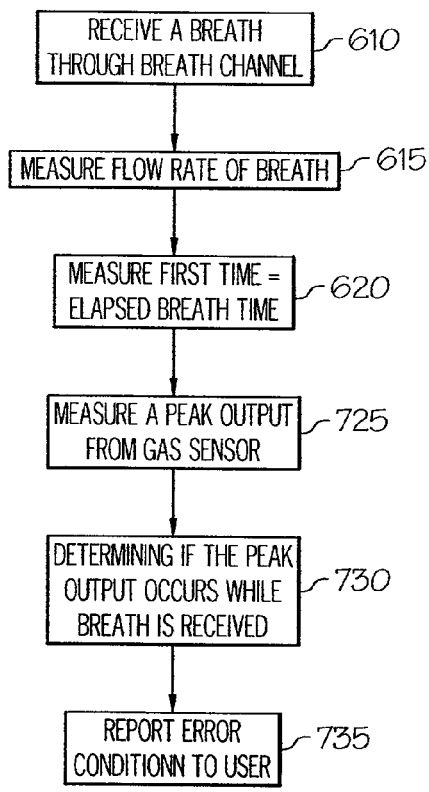
FIG. 4 is a flowchart depicting an exemplary method of detecting breath alcohol levels according to a fourth embodiment of the present invention.

In yet another exemplary embodiment illustrated in FIG. 4, the method further comprises: measuring a peak output from the gas sensor (step 725); and determining if the peak output from the gas sensor has occurred while breath is still being received in the breath channel (step 730). If breath is still being received and the peak output has occurred, the user is alerted of an error condition (step 735). In one exemplary embodiment, the determination of the peak output comprises comparison of at least one prior measured gaseous component level with the current measured gaseous component level. For example, if the current level is greater than the prior level, then the current level is saved as the peak output. This process continues until the current level drops below the saved peak output, meaning that the peak level has occurred. In another exemplary embodiment, the peak output is determined by what is commonly known as a peak-and-hold circuit. This circuit has an output that follows the gas sensor level as an input, but its output does not drop when the gas sensor input drops. Thus the circuit retains the peak gas sensor level.

One skilled in the art will appreciate the various components of the personal breath tester may be obtained from a multitude of sources known to those skilled in the art. For example, ethanol fuel cell sensors may be obtained from Guth Laboratories of Harrisburg, Pa. and from Draeger Safety of Houston, Tex. Typical microprocessors that may be utilized in the present invention may be obtained from Texas Instruments of Dallas, Tex. and Renesas of Santa Clara, Calif. Temperature sensors utilized in the present invention may be obtained from NIC of Melville, N.Y. and Murata of Smyrna, Ga.

The foregoing description of the exemplary embodiments has been presented for purposes of illustration and description. It is not intended to be exhaustive nor to limit the inventor to the precise form disclosed. Obvious modifications or variations are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

I claim:

1. A method for detecting gaseous component levels in a breath, comprising:
   receiving a breath through a breath channel, wherein the breath channel is in continuous fluid communication with a flow rate sensor and an electrochemical fuel cell gas sensor while the entire breath is received, and wherein the flow rate sensor and the electrochemical fuel cell gas sensor are in electrical communication with a processing device;
   measuring a flow rate of the breath received through the breath channel utilizing the flow rate sensor and transmitting a corresponding flow rate signal to the processing device;
   measuring a gas level of the breath received through the breath channel with the electrochemical fuel cell gas sensor and transmitting a corresponding gas level signal to the processing device;

measuring a first time, wherein the first time corresponds to an amount of time elapsed while receiving the breath in the breath channel;

calculating a current gaseous component level on the processing device utilizing the flow rate signal, the first time and the gas level signal from the gas sensor, wherein the gaseous component level is proportional to the gas level signal, the flow rate and the first time.

2. The method of claim 1, wherein the gaseous component is ethanol.

3. The method of claim 1, wherein the flow rate sensor comprises a pressure sensor.

4. The method of claim 1, wherein the flow rate sensor comprises a temperature sensor.

5. The method of claim 1, wherein calculating the current gaseous component level further comprises calculating a volume of breath received based on the flow rate signal and the first time.

6. The method of claim 5, further comprising measuring the flow rate at a plurality of time intervals; and calculating the volume of breath based on the plurality of flow rates and time intervals by integrating the flow rates over the time intervals.

7. The method of claim 1, further comprising determining if the gas level signal from the gas sensor is a peak gas level signal.

8. The method of claim 7, further comprising:

measuring a second time, wherein the second time corresponds to an elapsed time from the time corresponding to when the breath has ceased being received and the time corresponding to the peak gas level signal from the gas sensor;

wherein calculating the current gaseous component level further comprises utilizing the second time.

9. The method of claim 7, further comprising:

determining if the peak gas level signal occurs while breath is still being received in the breath channel; and if the peak gas level signal occurs while breath is still being received in the breath channel, alerting a user of an error condition.

10. A computer program product comprising a non-transitory computer readable medium carrying instructions for allowing a computer system to detect gaseous component levels in a breath received through a breath channel, the instructions comprising a method of: measuring a flow rate of the breath received through the breath channel utilizing a flow rate sensor in fluid communication with the breath channel and transmitting a corresponding flow rate signal to a processing device, wherein the processing device and the flow rate sensor are in electrical communication;

measuring a gas level of the breath received through the breath channel utilizing an electrochemical fuel cell gas sensor in continuous fluid communication with the breath channel while the entire breath is received and transmitting a corresponding gas level signal to the processing device, wherein the processing device and the electrochemical fuel cell gas sensor are in electrical communication;

measuring a first time, wherein the first time corresponds to an amount of time elapsed while receiving the breath in the breath channel;

calculating a current gaseous component level utilizing the flow rate signal, the first time and the gas level signal, wherein the current gaseous component level is proportional to the gas level signal, the flow rate and the first time.

11. The computer program product of claim 10, wherein calculating the current gaseous component level further comprises calculating a volume of breath received based on the flow rate signal and the first time.

12. The method of claim 11, further comprising measuring the flow rate at a plurality of time intervals; and calculating the volume of breath based on the plurality of flow rates and time intervals by integrating the flow rates over the time intervals.

13. The method of claim 10, further comprising determining if the gas level signal from the gas sensor is a peak gas level signal.

14. The method of claim 13, further comprising:

measuring a second time, wherein the second time corresponds to an elapsed time from the time corresponding to when the breath has ceased being received in the breath channel to the time corresponding to the peak gas level signal from the gas sensor;

wherein calculating the current gaseous component level further comprises utilizing the second time.

15. The method of claim 13, further comprising:

determining if the peak gas level signal occurs while breath is still being received in the breath channel; and if the peak gas level signal occurs while breath is still being received in the breath channel, alerting a user of an error condition.

\* \* \* \* \*